United States Patent [19]
Walker

[11] Patent Number: 6,102,888
[45] Date of Patent: Aug. 15, 2000

[54] METHOD OF IRRIGATING AND DRAINING URINARY TRACT

[76] Inventor: Frank J. Walker, 403 Lily Flagg Rd., SE., Huntsville, Ala. 35802

[21] Appl. No.: 08/906,721

[22] Filed: Aug. 5, 1997

Related U.S. Application Data

[62] Division of application No. 08/500,473, Jul. 10, 1995, Pat. No. 5,688,239.

[51] Int. Cl.[7] ........................................... A61M 1/00
[52] U.S. Cl. .............................. 604/28; 604/96; 604/264; 604/284
[58] Field of Search ................................ 604/28, 96, 264, 604/102, 280, 24

[56] References Cited

U.S. PATENT DOCUMENTS

| | | |
|---|---|---|
| 3,902,492 | 9/1975 | Greenhalgh . |
| 4,211,233 | 7/1980 | Lin . |
| 4,262,668 | 4/1981 | Schmidt . |
| 4,579,554 | 4/1986 | Glassman . |
| 5,007,897 | 4/1991 | Kalb et al. . |
| 5,306,241 | 4/1994 | Samples . |

FOREIGN PATENT DOCUMENTS

| | | |
|---|---|---|
| 449472 | 3/1981 | European Pat. Off. . |
| 3306342 | 2/1983 | Germany . |
| 2169206 | 7/1986 | United Kingdom . |
| 8811183 | 2/1988 | WIPO . |
| 8903232 | 4/1989 | WIPO . |
| 9218199 | 10/1992 | WIPO . |
| 9304727 | 3/1993 | WIPO . |

*Primary Examiner*—Wynn Wood Coggins
*Assistant Examiner*—N. Kent Gring
*Attorney, Agent, or Firm*—Lanier Ford Shaver & Payne P.C.; Frank M. Caprio; Russell L. Sandidge

[57] ABSTRACT

A urinary tract irrigating assembly for flushing a TURP-treated prostate gland having a surgically created central cavity. The assembly includes an elongated catheter having a drain port for draining the bladder contents; a discharge port for discharging prostate-irrigating fluid into the cavity; and a second drain port for draining spent prostate-irrigating fluid and other fluids from the cavity. Positioning means are provided for positioning the catheter with the first port located in the bladder and the second and third ports located within the prostate cavity. In use, a predetermined amount of irrigating fluid at predetermined time intervals is discharged into the prostate cavity through the discharge port while draining urine through the first drain port and spent prostate treating agent through the second drain port.

20 Claims, 5 Drawing Sheets

METHOD OF IRRIGATING AND DRAINING URINARY TRACT

This application is a division of application Ser. No. 08/500,473, filed Jul. 10, 1995, now U.S. Pat. No. 5,688,239.

FUNCTION

This invention relates to a urinary tract treating assembly for use in flush irrigating with an irrigating fluid a prostate gland having a central cavity created by surgical treatment. It relates further to a method of flushing such a cavity.

BACKGROUND OF THE INVENTION

As is well known, the aging process frequently results in enlargement of the prostate which, in turn, constricts the prostatic urethra as the gland enlarges. This often seriously restricts the urine flow to levels below that which is acceptable, or even blocks it altogether.

In the TURP surgical procedure (Transurethral Resection, Prostate) prostatic tissue is removed to enlarge the urethra where it passes through the prostate. This is one of the most common surgical procedures performed in the United States today, particularly upon male patients of advanced age.

Following the surgery, the urologist conventionally inserts a "3-way" catheter into the patient's bladder in order to drain the bladder of urine and any introduced irrigating fluid during the patient's postoperative recovery. While such a catheter effectively drains the contents of the bladder, it unfortunately does not have any provision for drainage of the prostate in order to remove blood and/or particles of excised prostatic tissue from the gland that actually experienced the operative trauma. However, the spent irrigant is collected and periodically examined visually by the surgeon as he follows the post operative progress.

I, the inventor herein, recently underwent a TURP procedure at a major medical center in a major metropolitan area. Following the operation, the usual 3-way catheter was inserted and the constant drip flow of irrigating fluid initiated into the bladder. Although bloody at first, the collected spent fluid (urine and normal saline solution irrigant) rather quickly became clear and remained clear for a day or two prior to my departure from the hospital.

As I was being prepared for departure, the catheter was routinely removed. Upon removal of the catheter I was amazed and shocked by the nature of the resulting flow of fluid from the penis inasmuch as it contained a large amount of totally unexpected semi-coagulated blood and other waste material. This was in sharp contrast to the clear liquid which had been discharged from the catheter during the previous day or two. Clearly, the traumatized prostate had not been flushed successfully by the irrigation procedure; this, in spite of the fact that the hospital financial statement which I received as I departed indicated that I had consumed over 20 3-liter bags of saline solution to irrigate the bladder, at a unit price of $51.75. Accordingly, I was charged over $1100.00 for irrigation supplies which had not achieved the desired purpose. Considering the tens of thousands of TURP operations that are performed in the United States each year, the resulting economic waste and financial burden needlessly placed upon the patient are staggering, not to mention the poor therapeutic results obtained by not irrigating the prostate following surgery.

Investigation quickly revealed the root of the problem. I asked the nurse to clean up the catheter and give it to me for inspection. Upon examination, I immediately realized that the catheter was designed in such a way that the irrigation fluid was introduced into the bladder, on which no surgery had been performed, as opposed to the prostate, which had been severely traumatized by the surgery, but did not directly receive any irrigation.

In effect, the irrigating fluid was merely "short circuited" through the bladder. Immediately after being discharged into the bladder it entered the adjacent bladder drain holes in the catheter provided for that purpose. Accordingly, only an extremely small percentage of the fluid ever reached the area it was intended to reach and where it was required, i.e. the traumatized prostate area. By reason of not having any provision for irrigation and drainage, the prostate area merely collected stale urine, undesired blood products etc. for the duration of the time that I wore the catheter.

The foregoing observation is confirmed by consideration of FIG. 6 of the drawings, illustrating schematically the construction and manner of use of the standard "3-way" catheter system used in my hospital and which, my urologist assured me, was also used universally by hospitals throughout the nation. I confirmed this conclusion by research through the voluminous catalogs of the major U.S. hospital supply distributors. All of them illustrated and offered for sale for use after prostate surgery only the "3-way" style urinary catheter illustrated in FIG. 6.

As shown schematically in that figure, the male urinary anatomy involved comprises the urethra 14, the prostate 16, the bladder neck 20 and the bladder 22. Following prostate surgery, the prostate is left with a central cavity 18 of surgically resected tissue, which is the area it is desired to irrigate and flush.

To accomplish the latter purpose, the prior art assembly employed in the hospital experience described above comprises an elongated catheter tube 24 equipped with positioning means comprising a conventional fluid-inflated "Foley" balloon 26.

The proximal end of the catheter has an irrigation port 28 connected to a source of irrigation fluid (drip bag). It also has one or more drain ports 30 and 31 which connect to a receiving receptacle for urine and spent irrigating fluid.

It is clearly evident from the foregoing why, in my hospital experience, the prostate cavity was inefficiently irrigated, if it was irrigated at all. The irrigating fluid was introduced into the bladder through port 28 and promptly exited through adjacent ports 30 and 31, completely bypassing the prostate area.

It is to be noted that in the use of this style catheter, the bladder is placed in an imperfectly sealed relation to the prostate cavity by means of locating balloon 26. The only way for blood, urine and surgical debris to be removed from the prostate area is for it to leak past the balloon and exit via ports 30 and 31 in the bladder. Such leakage is minimal, however, due to the complete lack of any catheter irrigation and/or drainage facilities within the prostate, as well as because of the sealing action of the locating balloon.

In addition to largely inhibiting the flow of irrigation fluid from the bladder to the prostate area, the imperfect seal created by balloon 26 has another adverse effect. It permits urine from the bladder to leak into the surgically resected prostate and accumulate there without there being any provision for drainage until the catheter ultimately is removed.

It is true that small amounts of urine and other fluids which accumulate in the prostate can, under some circumstances, leak past the circumferential fit between the catheter and the urethra downstream from the prostate, particularly if the catheter is a loose fit. However, such amounts are not sufficient to irrigate the prostate. Additionally in practice, this leakage is discouraged. Quite often provision is made to seal against it, inasmuch as it results in patient discomfort and soiling of his bedding and/or clothing.

In any event, such leakage generally is not relied upon as a primary means of draining the prostate. For all practical purposes, the prostate does not have any provision for drainage when the 3-way catheter is in place. Most of the stale urine, blood products and debris is left to accumulate in the prostate cavity. There it is subject to biological degradation, until withdrawal of the catheter several days following surgery.

Accordingly, what is required is an easily applied and serviced urinary catheter assembly which has provision for flushing out the prostate area quickly, repeatedly, effectively and safely. It is the general object of the present invention to provide such an assembly and a method for its application.

SUMMARY OF THE INVENTION

In the present invention, advantage is taken of the presence of surgically created cavity 18 centrally located in the prostate. The presence of this cavity makes it possible to overcome a primary problem which heretofore has attended prostate irrigation procedures and which presumably is responsible for the design of catheters having the characteristics and the mode of operation of that illustrated in FIG. 6.

The problem concerned is accurately set forth in Glassman U.S. Pat. No. 4,579,554, column 1, lines 42–51:

"All catheters previously designed to irrigate the penile urethra and provided with orifices situated at the base of the bladder are doomed to failure: first, the prostate gland is almost always hypertrophied and invariably the prostatic uretheral canal is so constricted that catheterization is required. To insert a catheter having perforations that rest within the prostate canal is to obviate the possibility of an irrigating fluid from escaping from the perforations into the prostatic canal."

The foregoing is not a problem when the patient has had a TURP operation with resultant formation of cavity 18 which now permits the flush irrigation of the prostate fossa effectively.

The herein described urinary tract treating assembly for flushing such a cavity with an irrigating fluid broadly comprises a catheter, a source of measured quantities of prostate-irrigating fluid under pressure, conduit means interconnecting the catheter and the source and valve means operatively associated with the conduit means for transmitting and applying to the cavity a predetermined amount of irrigating fluid at selected predetermined time intervals.

The catheter is schematically illustrated in FIG. 7 and is to be compared with the prior art catheter of FIG. 6, described above.

In catheter 32 of the invention, one or more urine drain ports 34 are provided at the proximal tip. These connect with a receiving receptacle at the other end of the catheter.

Also provided in the proximal portion of the catheter are a fluid dispensing port 36 and one or more spent fluid drain ports 38 positioned within the prostate cavity 18 by means of positioning balloon 62. This balloon is similar in construction and purpose to Foley balloon 26 of FIG. 6, previously described.

Fluid dispensing port 36 connects with a source of irrigation fluid under pressure associated with valving means for delivering the fluid to the prostate area in measured amount at predetermined intervals, as will be described in detail hereinafter.

Balloon 62 assures the proper positioning of the catheter with all three sets of ports in their desired operative positions, i.e. with urine drain port 34 in the bladder, and with both fluid dispensing port 36 and fluid drain port 38 in the prostate cavity. In this manner, efficient flush irrigating of the prostate is achieved, while retaining effective drainage of the bladder.

DETAILED DESCRIPTION OF PREFERRED EMBODIMENTS OF THE INVENTION

Figure 1:
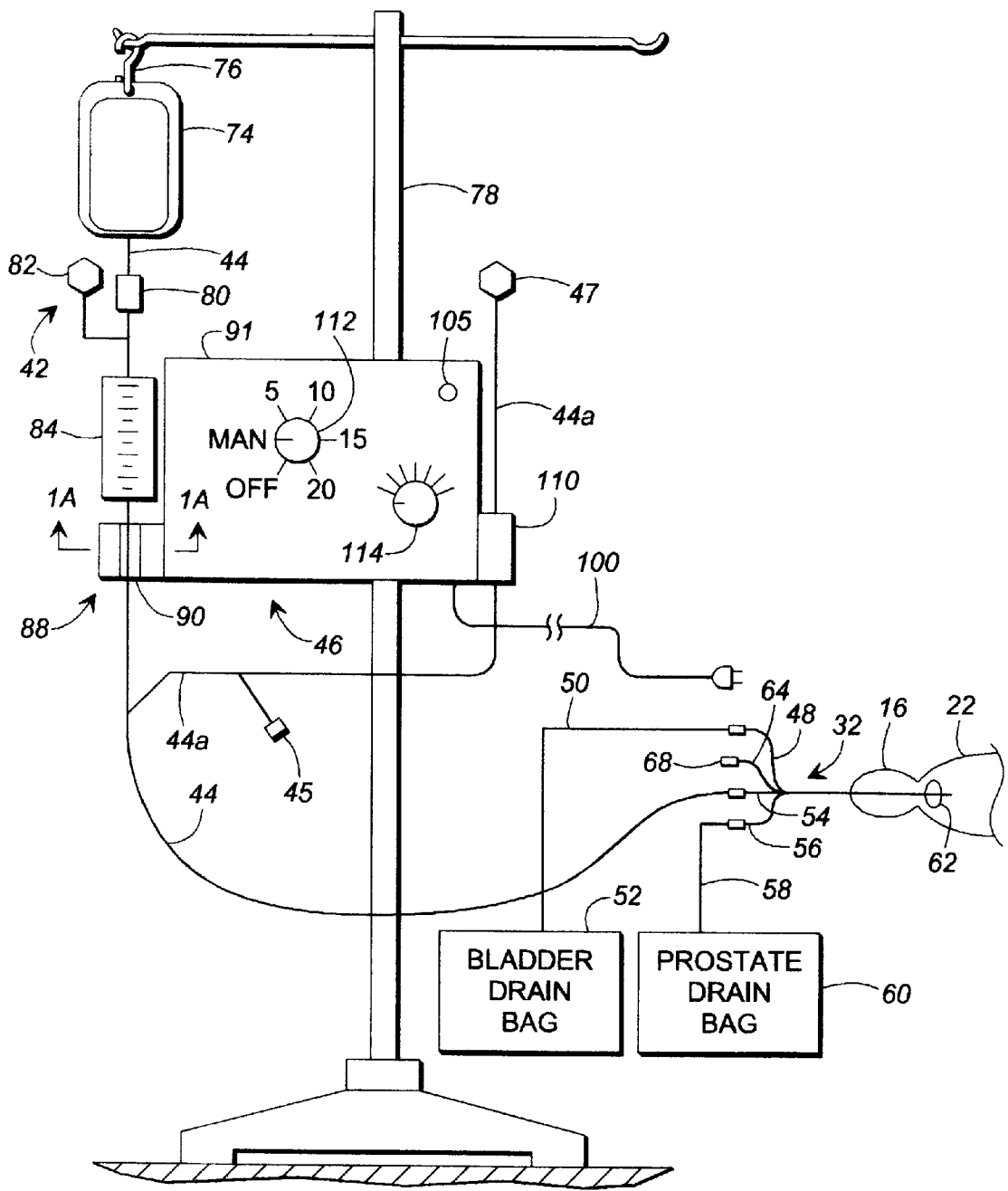
FIG. 1 is a schematic view in elevation of apparatus for supplying prostate irrigating fluid to the urinary catheter of the invention, in measured amount at predetermined time intervals.

The urinary tract treating assembly of my invention is schematically illustrated in FIG. 1. It broadly comprises a catheter, indicated generally at 32; a source 42 of measured quantities of prostate-irrigating fluid under pressure, for example that provided by a gravitationally produced hydrostatic pressure; conduit means 44 interconnecting the catheter and the source; and valve means with associated control means, indicated generally at 46, for transmitting and applying to the prostatic cavity a predetermined amount of irrigating fluid at predetermined time intervals.

The construction and mode of operation of catheter 32 are illustrated in FIGS. 3, 4, 4a, 4b and 5.

As illustrated, the catheter may be fabricated by extrusion, molding, dipping or other suitable procedure from a unitary piece of suitable material, preferably medical grade silicone. It has a proximal portion, which lies to the right as viewed in FIG. 3, and a branched distal end, which lies to the left as viewed in that figure.

In the proximal portion are located one or more bladder drain ports 34, one or more prostate cavity irrigation ports 36, and one or more prostate cavity drain ports 38. The branched distal ends are open except for branch 64 which contains balloon (Foley) inflation valve 68, generally a medical Luer lock device.

Three longitudinally arranged conduits are molded into or mounted longitudinally of the catheter. These have proximal and distal portions corresponding to the proximal and distal portions of the catheter.

The distal ends are open and outwardly flared to provide lumens for connection to connecting tubing, as will appear hereinafter.

The first catheter conduit 34, 48, is the bladder drain conduit. Urine enters through port 34, drains the length of conduit 48, and is discharged through the open distal end of the latter. It thereupon is transferred by means of tube 50 to a suitable receptacle such as a transparent plastic bladder drain bag 52, FIG. 1, located on the patient's bed.

The second conduit 36, 54, functions to discharge prostate-irrigating fluid into prostate cavity 18. Its open distal end is connected via conduit means 44, to a source of irrigating fluid under pressure. This pressure typically is determined by the difference in static elevation of the fluid reservoir 84 and the prostate cavity 18. The fluid travels the length of conduit 54 and is discharged through port 36 into the prostate cavity 18.

The third catheter conduit 38, 56 has for its function draining the spent irrigation fluid and other fluids from the prostate cavity. Its open distal end is connected to a tube 58 which conveys the spent irrigating fluid to a suitable transparent plastic receptacle such as prostate drain bag 60.

Figure 7:
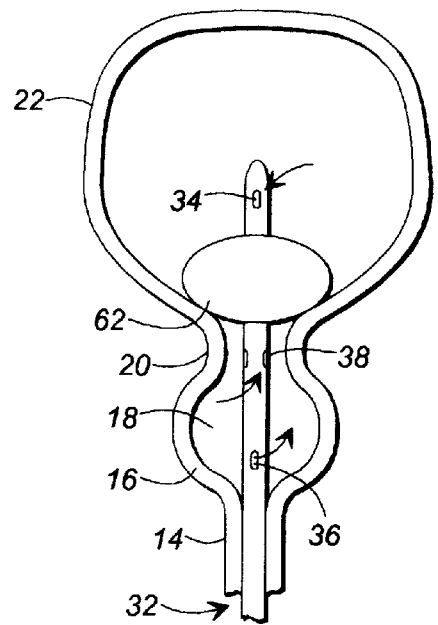
FIG. 7 is a schematic diagram of the male urinary tract similar to FIG. 6, but with the presently described combination bladder drain and prostate irrigation and drain catheter in place.

Catheter positioning means are provided for positioning the catheter in its operative position with urine drain ports 34 positioned in the bladder and with prostate irrigation fluid discharge and drain ports 36, 38 being positioned in surgically-created prostrate cavity 18, as illustrated in FIG. 7.

Although various positioning means may be provided for this purpose, it is preferred to use the well known "Foley" balloon catheter positioning means which has been referred to hereinabove. The construction of this conventional device is indicated in FIG. 3.

The balloon comprises an expandable segment, indicated in its collapsed condition in full outline at 62. In its expanded condition it is indicated in dashed outline 62.

Figure 3:
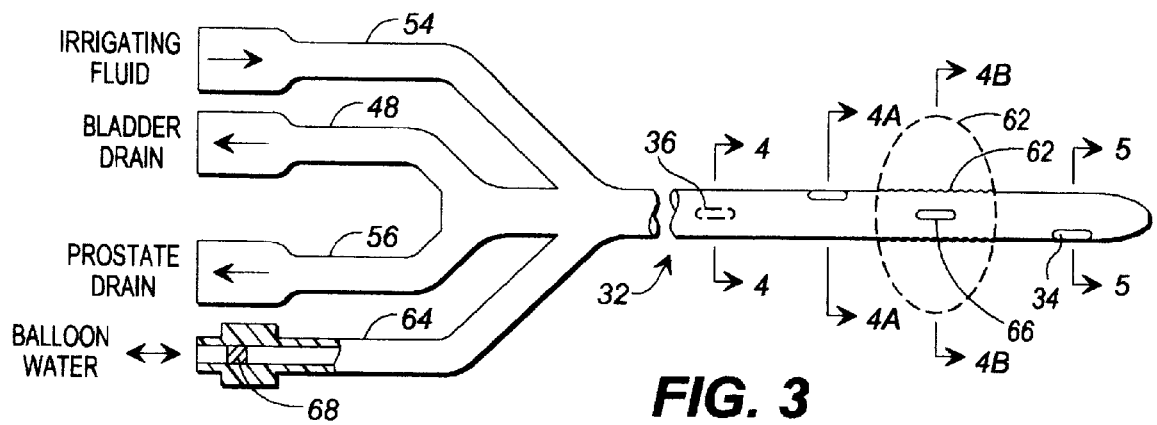
FIG. 3 is a fragmentary, schematic diagram of the catheter component of the apparatus in a first embodiment.
Figure 4:
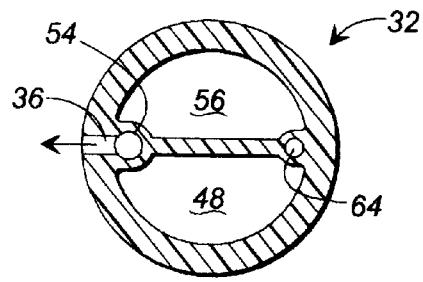
FIGS. 4, 4A, 4B and 5 are transverse sectional views taken along lines 4—4, 4A—4A, 4B—4B, and 5—5 of FIG. 3.
Figure 4A:
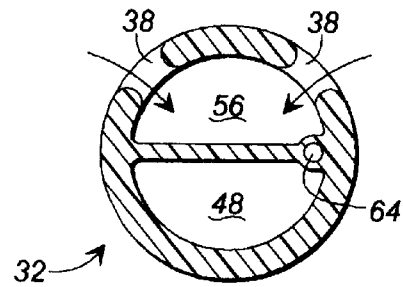
Figure 4B:
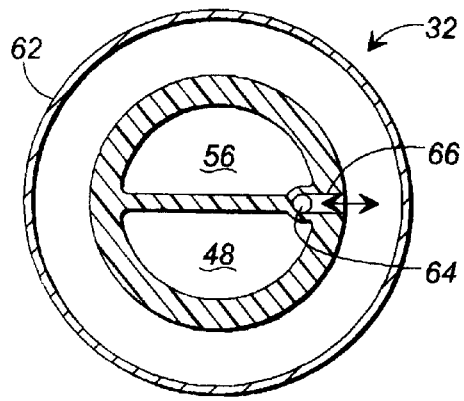
Figure 5:
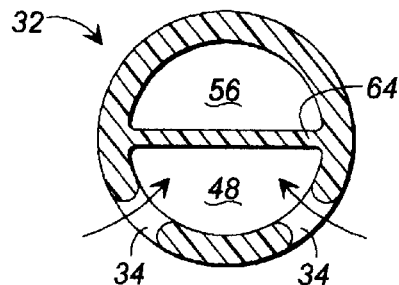
Figure 6:
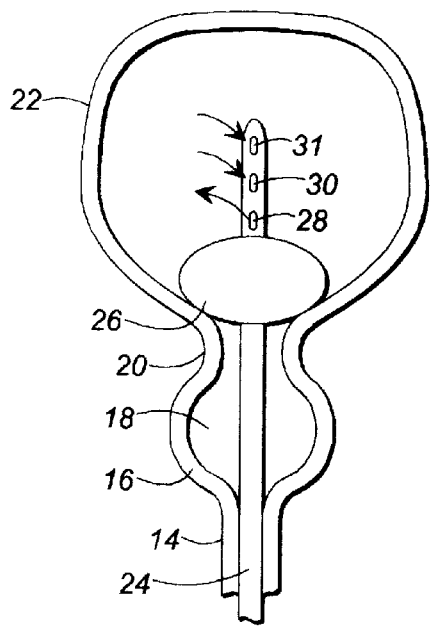
FIG. 6 is a schematic diagram of a portion of the male urinary tract with a schematic prior art combination of bladder irrigating and drain catheter in place.

Balloon 62 is designed to be converted from its collapsed condition to its expanded condition by filling it with sterile water, which thereafter can be drained to restore the balloon to its collapsed, full line condition of FIG. 3.

To accomplish this conversion, there is provided a fourth catheter conduit 64 which extends the length of the catheter and terminates in one or more openings or ports 66. The open distal end of conduit 64 is provided with a water-tight device 68 which is generally a conventional Luer lock that can be manually held open to either inflate or deflate the balloon with an appropriate Luer lock actuator, such as a Luer-equipped medical syringe. The conduit, and hence balloon 62, can be filled and emptied in this manner.

An alternate catheter construction is illustrated in FIGS. 8–12, inclusive. It has for its purpose the provision of a drain conduit of enlarged cross section, thus minimizing the possibility of the catheter being clogged by an accumulation of coagulated blood and/or surgically resected debris.

This purpose is accomplished by combining bladder drain conduit 48 and prostate drain conduit 56 into a single drain conduit 70 of increased cross section and higher flow capacity.

Such a combination obviously might afford access of spent prostate irrigation fluid to urine drain openings 34, located in the bladder. However, one way valve means 72 is provided to prevent such access.

Figure 9:
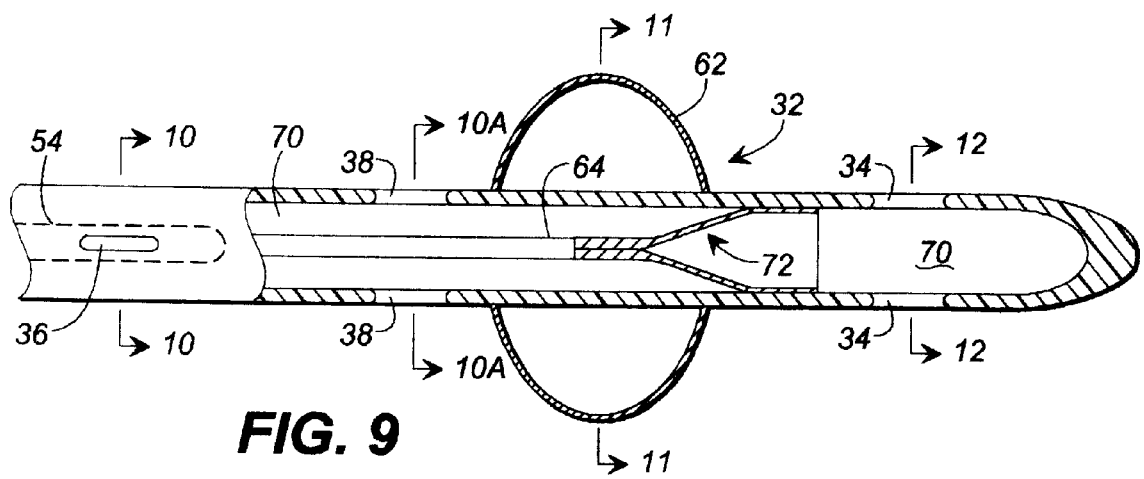
FIG. 9 is a fragmentary, longitudinal sectional view taken along the line 9—9 of FIG. 8.
Figure 10:
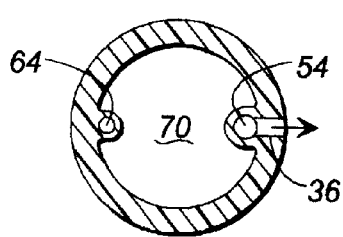
FIGS. 10, 10A, 11 and 12 are transverse sectional views taken along lines 10—10, 10A—10A, 11—11 and 12—12 of FIGS. 8 and 9.
Figure 10A:
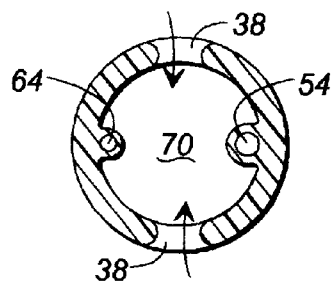
Figure 11:
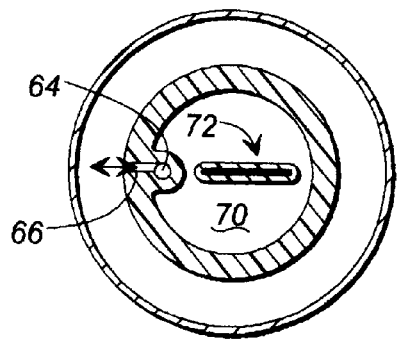
Figure 12:
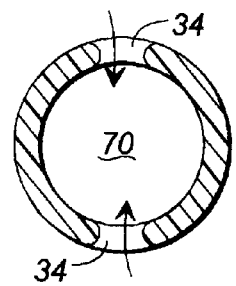

In the illustrated form of the invention, FIG. 9, the one way valve means employed is a flattened flap-type valve 72 of resilient tubing. This valve has a contour and construction such that its flattened distal end portion is maintained resiliently closed, while its proximal end portion is maintained fixed in the open condition and attached to the inner wall of catheter 32. Accordingly, urine from the bladder can flow in the downstream direction into enlarged drain conduit 70, where it mixes with the spent irrigation fluid entering the conduit through drain ports 38. The mixture then flows to the open distal end of conduit 70, where it discharges into means for conveying it to a suitable storage receptacle, not illustrated, but common to both both bladder and prostate effluents.

Figure 8:
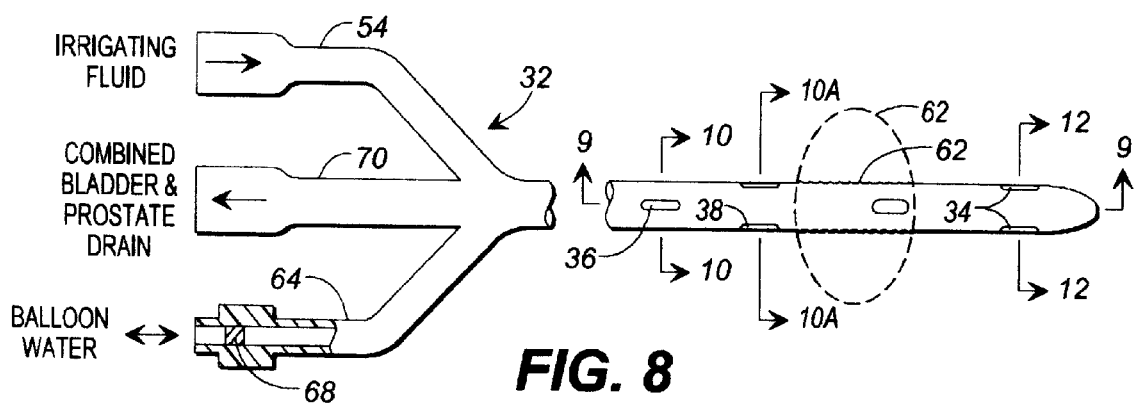
FIG. 8 is a fragmentary, schematic view of the herein described catheter component of the assembly in a second embodiment.

In either embodiment, i.e. that of FIG. 3 or that of FIG. 8, the open distal end of irrigation fluid conduit 54 is connected to a source of irrigation fluid under pressure, delivered in measured amount on a predetermined time schedule. The manner in which this is accomplished is illustrated in FIGS. 1, 1A, 1B and 2.

As shown in FIG. 1, the source of irrigation fluid under a hydrostatic head of pressure comprises a collapsible bag 74 filled with the irrigating fluid and suspended by hook 76 from a conventional "I.V. Pole" 78. The collapsible bag discharges into a flow regulating clamp 80 which is used to regulate the rate of flow of irrigant as it refills reservoir 84 between flushes. Combination air vent and check valve 82 prevents "air lock" and permits graduated fluid reservoir 84 to empty quickly when pinch valve 88 is opened. There thus is provided a means of accumulating a measured amount of irrigation fluid to be released periodically for flushing out the prostate cavity with a rush of irrigant, as opposed to the relatively ineffective prior art procedure of dripping the fluid a drop at a time into the bladder.

Figure 1A:
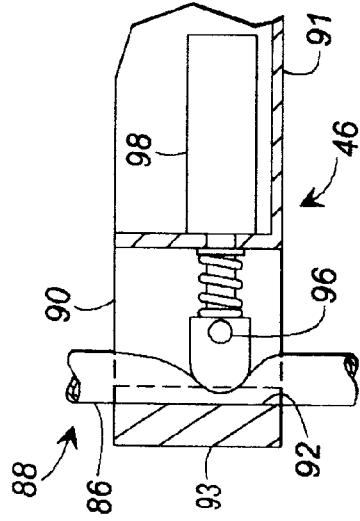
FIG. 1A is a fragmentary, detailed, sectional view of valve means employed in the apparatus of FIG. 1, taken along line 1A—1A of FIG. 1.
Figure 1B:
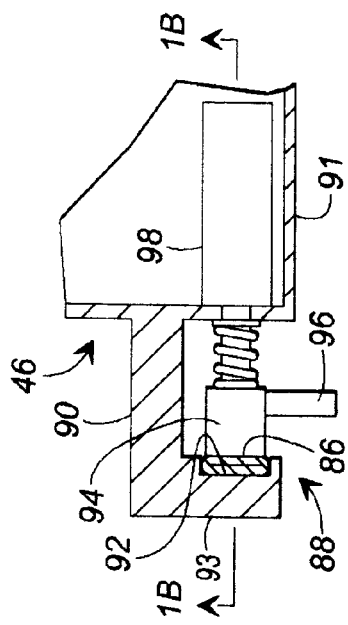
FIG. 1B is a detailed, fragmentary, sectional view taken along line 1B—1B of FIG. 1A.

The valve means employed for periodically releasing the measured contents of reservoir 84 is illustrated in FIGS. 1, 1A, and 1B.

Conduit 44 with branch 44a (vented at 47) interconnects the downstream end of calibrated reservoir 84 with the open distal end of catheter conduit 54, which supplies irrigation fluid to the prostatic cavity via discharge port 36. An injectable side port 45 is provided in branch conduit 44a. This serves the function of permitting medical personnel to syringe-inject antibiotics and other special medication into catheter conduit 44, without disconnecting the conduit.

Connecting conduit 44 includes a length 86 of thin wall resilient tubing made of a resilient plastic such as silicone, or other suitable resilient material. Pinch clamp means 88 are provided for alternately pinching off and opening the tubing segment in accordance with the desired time sequence.

The pinch clamp means comprises a bracket 90 mounted on control box 91 and having a recess 92 dimensioned to receive the tubing segment. The bracket is of reasonably substantial construction and has an abutment wall 93 against which works a spring-pressed, reciprocating ram 94.

Both manual mechanical and automated electronic means are provided for reciprocating the ram between its positions of valve opening and valve closing.

The manual mechanical means employed for this purpose comprises a simple lever 96 fixed to the head of the ram. By means of the lever, the ram can be retracted to open the valve, but against the tension of its associated spring. Upon release of the lever, the spring acts to close the valve.

The automated electronic means for operating the ram comprises an electrically operated "pull" solenoid 98, arranged as shown in FIGS. 1A and 1B to open the valve against the compression of the valve spring. The latter member then returns the valve to its closed position upon deenergization of the solenoid. This shuts off the flow of irrigant.

Figure 2:
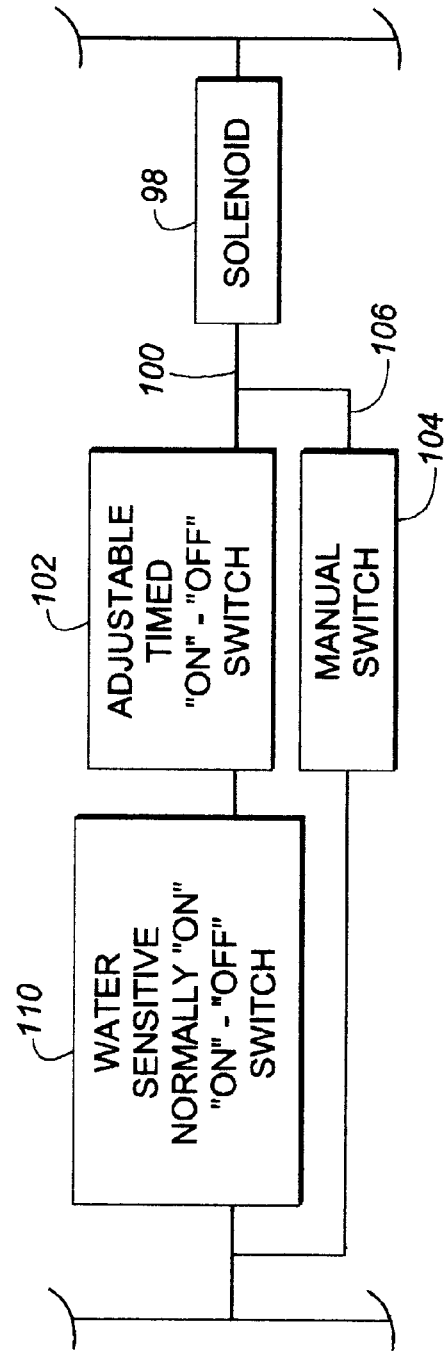
FIG. 2 is a schematic diagram of the electronic controls for the apparatus of FIG. 1.

A simple circuit for operation of the solenoid is illustrated in FIG. 2.

As therein depicted, the electric circuit 100 (preferably 12 VDC for patient safety), includes in series circuit relationship solenoid 98 and a adjustable, timed, on-off switch 102 for the operation of the same. If desired, in a shunt circuit 106 there may also be included a manual electric switch 104. This serves the same purpose as lever arm 96 on spring pressed ram 94, in permitting a single operation of the valve when electrically actuated.

Following prostate surgery, it frequently occurs that the patient's catheter becomes clogged with blood clots and surgical debris, or that drain conduit 58 becomes kinked, shutting off the flow. If either of these contingencies occurs, and if the supply of irrigating fluid is continued, pressure will build up in the urinary tract, resulting in severe (and even dangerous) patient discomfort.

If this event occurs in the use of the presently described apparatus, the irrigant will back up in conduit 44 and enter branch conduit 44a. To arrest the further flow of irrigant, there is provided in branch conduit 44a a water sensitive, normally "on", "on-off" switch 110. This switch is in series in circuit 100 with switch 102. If aqueous irrigant such as normal saline solution enters switch 110, the solenoid circuit immediately is interrupted. This closes pinch valve 88, and arrests the further flow of irrigant. Simultaneously, it turns on a flashing indicator light and an audible alarm buzzer (not depicted) to alert the patient and/or medical personnel that a catheter blockage has occurred. Upon clearing the blockage, the light and audible alarm turn off and normal periodic flow of the irrigant is again restored automatically.

As shown schematically in FIG. 1, the electronic elements of the control assembly are housed in, or mounted on, control box 91, which also mounts pinch clamp valve 88. In FIG. 1, the numerals 112, 114 indicate, respectively, the time interval and flow duration control knobs for adjustable, timed "on-off" switch 102. The numeral 105 indicates the control knob for manual switch 104.

OPERATION

The operation of the above described urinary tract treating assembly is as follows:

After hanging irrigation fluid bag 74 on pole 78, the operator connects the bag to the upstream end of conduit 44 in a conventional manner. Flexible segment 86 of the conduit is positioned in recess 92 of bracket 90 after retracting spring-pressed ram plunger 94. Ram 94 is designed to be operated either manually by means of lever 96, or electronically by means of solenoid 98, upon energization by operation of (control knob 112) either adjustable, timed on-off switch 102 or manual electric switch 104.

Drip-regulating clamp 80 is opened and reservoir 84 permitted to fill. When it is filled to the desired level and the desired time interval has elapsed, valve 88 is actuated either manually or electronically. Thereupon the charge of irrigation fluid flows through conduit 44 and into catheter conduit 54. The flow exits the latter conduit via irrigation port 36. It flushes out the surgically created prostate cavity 18 with a rush of fluid, thereby cleaning it effectively. The spent irrigation fluid exits via drain port 38 in prostate drain conduit 56. From there it flows into prostate drain bag 60 for examination and disposal.

In the meantime, and continuously, urine drains from bladder 22 through bladder drain port 34 into bladder drain 48. From there, the urine drains into bladder drain bag 52.

The operation is similar when the consolidated catheter embodiment of FIGS. 8–12 is employed. However in this case, the urine and spent irrigation fluid exit the catheter via a common conduit 70. The urine, entering the catheter through drain port 34 passes through one way valve 72 and thence into downstream conduit 70. The irrigation fluid enters prostate cavity 18 through port 36, and discharges through ports 38 into common conduit 70.

As an alternative mode of operation, clamp 80 and valve 88 may be left in their open positions and a drip of controlled rate initiated by regulating valve 80. Reservoir 84 then serves as drip chamber to confirm visually the selected drip rate. Antibiotics or other medicinal substances may be introduced as desirable or necessary through side port 45 in conduit 44a.

The assembly thus may be operated automatically over long operating periods. In the event of an inadvertent malfunction, such as one caused by clot-blockage of the catheter, or kinking, or clot blockage of conduit 58, water-sensitive switch 110 will terminate the flow of irrigant. The patent's comfort and safety thus are assured.

Having thus described in detail a preferred embodiment of the present invention, it will be apparent to those skilled in the art that many physical changes may be made without altering the inventive concepts and principles embodied therein. The present embodiments therefore are to be considered in all respects as illustrative and not restrictive, the scope of the invention being indicated by the appended claims.

I claim:

1. A method of irrigating and draining a urinary tract having a bladder and a prostate cavity, the method comprising the steps of:
    (a) providing an elongated catheter having a bladder drain conduit, an irrigation conduit, and a prostate drain conduit;
    (b) draining the contents of the bladder through the bladder drain conduit;
    (c) irrigating the prostate cavity with fluid discharged through the irrigation conduit; and
    (d) draining the irrigating fluid from the prostate cavity through the prostate drain conduit.

2. The method of claim 1, wherein the step of providing an elongated catheter includes providing an elongated catheter having a bladder drain conduit defining a bladder drain port.

3. The method of claim 1, wherein the step of providing an elongated catheter includes providing an elongated catheter having an irrigation conduit defining an irrigation port.

4. The method of claim 1, wherein the step of providing an elongated catheter includes providing an elongated catheter having a prostate drain conduit defining a prostate drain port.

5. The method of claim 1, further comprising the step of positioning the catheter within the urinary tract.

6. The method of claim 5, wherein the step of positioning the catheter includes inflating a balloon positioned along the length of the catheter.

7. The method of claim 1, further comprising the step of positioning the catheter within the urinary tract so that the bladder drain conduit is in fluid communication with the bladder, and so that the fluid discharge conduit and the prostate drain conduit are in fluid communication with the prostate cavity.

8. The method of 1, wherein the step of irrigating the prostate cavity includes delivering a measured amount of fluid according to a pre-determined time schedule.

9. The method of claim 1, further comprising the step of connecting a drain bag to the bladder drain conduit.

10. The method of claim 1, further comprising the step of connecting a drain bag to the prostate drain conduit.

11. A method of irrigating and draining a urinary tract having a bladder and a prostate cavity, the method comprising the steps of:

(a) providing an elongated catheter having a drain conduit defining a first port for draining the bladder and a second port for draining the prostate cavity, and having an irrigation conduit;

(b) draining the contents of the bladder through the drain conduit;

(c) irrigating the prostate cavity with fluid discharged through the irrigation conduit; and (d) draining the irrigating fluid from the prostate cavity through the prostate drain conduit second port.

12. The method of claim 11, further comprising the step of positioning the catheter within the urinary tract.

13. The method of claim 12, wherein the step of positioning the catheter includes inflating a balloon positioned along the length of the catheter.

14. The method of claim 11, further comprising the step of positioning the catheter within the urinary tract so that the first port of the drain conduit is in fluid communication with the bladder, and so that the second port of the drain conduit is in fluid communication with the prostate cavity.

15. The method of claim 11, further comprising the step of connecting a drain bag to the drain conduit.

16. The method of claim 15, further comprising the step of collecting urine and irrigant discharge in the drain bag connected to the drain conduit.

17. The method of claim 11, wherein the step of providing an elongated catheter includes providing a catheter having a one-way valve positioned within the catheter between the first port and the second port.

18. The method of 11, wherein the step of irrigating the prostate cavity includes delivering a measured amount of fluid according to a pre-determined time schedule.

19. The method of flushing with a prostate irrigating fluid a TURP-treated prostate gland having a surgically-created central cavity, the method comprising providing catheter means connected to a source of irrigating fluid under pressure and a receptacle for receiving spent treating fluid, the catheter means having an irrigating fluid discharge port and a spent fluid drain port, arranging the catheter means in the urethra with both ports operatively positioned in the prostatic cavity, discharging into the cacity through the discharge port a predetermined amount of irrigating fluid at predetermined time intervals, draining spent irrigating fluid from the cavity through the drain port, and transmitting the same to the spent treating fluid receptacle.

20. The method of claim 19 including the step of arranging the catheter means with the drain port proximal to the discharge port and flushing the cavity in the proximal direction.

* * * * *